United States Patent
Ray et al.

(10) Patent No.: US 11,040,118 B2
(45) Date of Patent: Jun. 22, 2021

(54) IN-VIVO REACTIVE SPECIES IMAGING

(71) Applicant: Caliper Life Sciences, Inc., Waltham, MA (US)

(72) Inventors: Sunetra Ray, Fremont, CA (US); Daniel Ansaldi, Alameda, CA (US); Rajendra Singh, San Jose, CA (US)

(73) Assignee: Caliper Life Sciences, Inc., Waltham, MA (US)

( * ) Notice: Subject to any disclaimer, the term of this patent is extended or adjusted under 35 U.S.C. 154(b) by 0 days.

(21) Appl. No.: 16/182,941

(22) Filed: Nov. 7, 2018

(65) Prior Publication Data
US 2019/0070317 A1   Mar. 7, 2019

Related U.S. Application Data

(62) Division of application No. 14/030,428, filed on Sep. 18, 2013, now Pat. No. 10,124,072.

(51) Int. Cl.
*A61K 49/00* (2006.01)

(52) U.S. Cl.
CPC ...... *A61K 49/0052* (2013.01); *A61K 49/0019* (2013.01); *A61K 49/0058* (2013.01); *A61K 49/0093* (2013.01)

(58) Field of Classification Search
None
See application file for complete search history.

(56) References Cited

U.S. PATENT DOCUMENTS

| | | |
|---|---|---|
| 5,108,899 A | 4/1992 | Allen |
| 5,340,716 A | 8/1994 | Ullman et al. |
| 6,251,581 B1 | 6/2001 | Ullman et al. |
| 6,406,913 B1 | 6/2002 | Ullman et al. |
| 6,692,975 B2 | 2/2004 | Singh et al. |
| 6,916,667 B2 | 7/2005 | Singh et al. |
| 7,179,660 B1 | 2/2007 | Kirakossian et al. |
| 7,842,823 B2 | 11/2010 | Chang |
| 8,795,731 B1 | 8/2014 | Perez et al. |
| 10,124,072 B2 | 11/2018 | Ray et al. |
| 2010/0069726 A1 | 3/2010 | Levinson |
| 2011/0250145 A1 | 10/2011 | Sharma et al. |
| 2013/0101511 A1 | 4/2013 | Ansaldi et al. |

FOREIGN PATENT DOCUMENTS

| | | |
|---|---|---|
| CN | 101183073 | 5/2008 |
| EP | 0 515 194 | 11/1992 |
| WO | WO 01/67105 | 9/2001 |
| WO | WO 2005/094902 | 10/2005 |
| WO | WO 2006/064453 | 6/2006 |
| WO | WO 2010/040062 | 4/2010 |
| WO | WO 2010/143942 | 12/2010 |

OTHER PUBLICATIONS

Biju et al., "Bioconjugated quantum dots for cancer research: Present status, prospects and remaining issues", *Biotechnology Advances*, vol. 28, No. 2, pp. 199-213 (2010).
Bilyy et al, "Detection of dying cells using lectin-conjugated fluorescent and luminescent nanoparticles", *Mat.-wiss. U. Werkstofftech.*, vol. 40, No. 4, pp. 234-237 (2009).
First Office Action for Chinese Patent Application No. 201480051542.X dated Jul. 2, 2018 (pages).
International Preliminary Report on Patentability and Written Opinion of the International Searching Authority dated Mar. 31, 2016 (8 pages).
International Search Report and the Written Opinion of the International Searching Authority for International Application No. PCT/US2014/056292 dated Jan. 22, 2015 (14 pages).
Gao et al., "In vivo molecular and cellular imaging with quantum dots", *Current Opinion in Biotechnology*, vol. 16, No. 1, pp. 63-72 (2005).
Roda et al., "Chemiluminescent Imaging of Enzyme-Labeled Probes Using an Optical Microscope Videocamera Luminograph", *Analytical Biochemistry*, Article No. AB972514, vol. 257, No. 1, pp. 53-62 (1998).
Song et al., "A Europium(III) Complex as an Efficient Singlet Oxygen Luminescence Probe", *J. Am. Chem. Soc.*, vol. 128, pp. 13442-13450 (2006).
Uusitalo, Larissa M. et al., "Recent Advances in Intracellular in In Vivo ROS Sensing: Focus on Nanoparticle and Nanotube Applications," *Int. J. Mol. Sci.* 13: 10660-10679 (2012).
Zhang, Ning et al., "Enhanced detection of myeloperoxidase activity in deep tissues through luminescent excitation of near-infrared nanoparticles," *Nature Medicine* 19: 500-505 (2013).

*Primary Examiner* — Jennifer Lamberski
(74) *Attorney, Agent, or Firm* — Fish & Richardson P.C.

(57) ABSTRACT

The disclosure features methods that include: administering to a subject a composition that includes particles, where each one of the particles features at least one targeting group that binds to a structural entity in the subject and at least one reacting group that reacts chemically with a reactive oxygen species in the subject, and where the particle emits luminescence when the reaction occurs; detecting the luminescence emission from the particles; and displaying an image of the subject showing locations of at least some reactive oxygen species in the subject based on the detected luminescence.

13 Claims, 11 Drawing Sheets

C28 thioxene

IN-VIVO REACTIVE SPECIES IMAGING

CROSS REFERENCE TO RELATED APPLICATIONS

This application is a division of and claims priority under 35 U.S.C. § 120 from U.S. application Ser. No. 14/030,428 filed on Sep. 18, 2013, the entire contents of which is incorporated herein by reference in its entirety.

TECHNICAL FIELD

This disclosure relates to imaging of reactive oxygen species, including imaging in living subjects.

BACKGROUND

Reactive oxygen species (ROS) are implicated in a variety of biological functions. For example, intracellular changes in ROS can influence cell signaling by thiol oxidation within target proteins, resulting in changes that affect the structure-function properties of the proteins. Oxidation by ROS has also been attributed to activating kinases and inhibiting phosphatases, leading to enhancement of phosphorylation cascades. Conformational changes due to oxidation by ROS can also result in changes in protein stability, protein-protein and protein-DNA interactions, and subcellular localization. Redox regulation, in which ROS play a role, has been attributed to various signaling pathways and may affect cellular responses such as transcription regulation, proliferation, migration, metabolism, survival and inflammatory response.

SUMMARY

Redox signaling in cells depends on the balance between in-vivo production of ROS, and scavenging of excess ROS by intracellular antioxidant species ROS sources include NADPH oxidases and mitochondria (e.g., the mitochondrial electron transport chain). NADPH oxidases produce superoxide ($O_2^-$), which is rapidly converted to hydrogen peroxide ($H_2O_2$) by superoxide dismutases. When a subject is affected by certain pathophysiological conditions such as cancer and inflammatory disease, aberrant redox signaling often accompanies other symptoms of the condition. Aberrant redox signaling, in turn, may be the result of disruption of the balance between ROS production and ROS scavenging by antioxidant species. In particular, enhanced production of ROS in diseased tissue and/or reduced production of antioxidant species such as superoxide dismutases, catalase, glutathione peroxidase, thioredoxin, peroxiredoxin, and/or the glutathione family, can lead to such imbalances. As a result, localization and quantification of ROS in-vivo can provide important diagnostic information for identifying various cancers and inflammatory conditions.

In general, in a first aspect, the disclosure features methods that include: administering to a subject a composition that includes particles, where each one of the particles features at least one targeting group that binds to a structural entity in the subject and at least one reacting group that reacts chemically with a reactive oxygen species in the subject, and where the particle emits luminescence when the reaction occurs; detecting the luminescence emission from the particles; and displaying an image of the subject showing locations of at least some reactive oxygen species in the subject based on the detected luminescence.

Embodiments of the methods can include any one or more of the following features.

Administering the composition can include injecting the particles in a body of the subject. The subject can be a living human. The subject can be a living mammal (e.g., a mouse, a rat). The subject can be a living bird, a living amphibian, or a living fish.

The methods can include detecting luminescence emission at a wavelength of 500 nm or more (e.g., 600 nm or more, 700 nm or more). The methods can include displaying the image of the subject based on unfiltered emitted radiation from the subject, where the unfiltered emitted radiation includes the luminescence emission.

The at least one targeting group can include at least one antibody. The reactive oxygen species can include singlet oxygen and/or hydroxide radical and/or hypochlorous acid and/or superoxide radical and/or nitric oxide and/or hydrogen peroxide.

Each one of a first subset of the particles can include a first targeting group and a first reacting group, and each one of a second subset of the particles can include a second targeting group and a second reacting group, where the first and second targeting groups are different. The first and second targeting groups can bind to different structural entities in the subject. The first and second targeting groups can include different antibodies.

Each one of the first subset of the particles can emit luminescence at a first central wavelength, and each one of the second subset of the particles can emit luminescence at a second central wavelength different from the first central wavelength. Each of the first and second central wavelengths can be greater than 500 nm.

The first and second reacting groups can be the same.

Embodiments of the methods can also include any of the other features or steps disclosed herein, in any combination, as appropriate.

In another aspect, the disclosure features compositions that include a suspension medium and a plurality of particles, where each one of the plurality of particles features: a core that includes at least one reacting group that reacts chemically with a reactive oxygen species in the subject, and at least one luminescent agent that emits luminescence in response to the reaction of the at least one reacting group; a first coating material encapsulating the core; and a second coating material encapsulating the first coating material and including at least one targeting group that binds to a structural entity in the subject.

Embodiments of the compositions can include any one or more of the following features.

The core can include at least one of latex and polystyrene. The first coating material can include aminodextran and the second coating material can include dextran aldehyde.

The at least one targeting group can include at least one antibody. The at least one luminescent agent can include at least one lanthanide element. The at least one lanthanide element can include at least one of europium and terbium. The at least one reacting group can include thioxene or a thioxene derivative.

The plurality of particles can include: a first subset of particles featuring a first targeting group, a first luminescent agent, and a first reacting group; and a second subset of particles featuring a second targeting group, a second luminescent agent, and a second reacting group, where the first and second targeting groups are different. The first and second targeting groups can include different antibodies.

The first and second luminescent agents can be different. The first and second luminescent agents can include different lanthanide elements.

Any one or more of the compositions disclosed herein can be included in a kit for imaging reactive oxygen species in a living subject. The reactive oxygen species can include at least one member selected from the group consisting of singlet oxygen, hydroxide radical, hypochlorous acid, superoxide radical, nitric oxide, and hydrogen peroxide.

Embodiments of the compositions can also include any of the other features disclosed herein, in any combination, as appropriate.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

Like reference symbols in the various drawings indicate like elements.

DETAILED DESCRIPTION

Reactive oxygen species (ROS) have been detected using combinations of different types of particles. In particular, combinations of donor and acceptor beads have been used as in-vitro ROS sensors. Typically, the donor and acceptor beads are brought into proximity by an analyte in a sandwich where illuminating the donor particles at the wavelength of the sensitizer generates singlet oxygen or other ROS. ROS thus generated chemically react with an electron rich olefin or reactive oxygen sensor in the acceptor beads, which emit light following the reaction. The emitted light from the acceptor beads can be transferred to an appropriate acceptor in a FRET manner which can be imaged or read in the plate reader.

In general, the acceptor beads are able to sense ROS only within a finite distance as ROS decay rapidly within their lifetime of approximately 2 microseconds. For example, singlet oxygen typically traverses distance of only about 200 nm before it decays. As a result, efficient excitation of an acceptor bead by a donor bead typically occurs when the acceptor and donor beads approach relatively closely (e.g., within a few hundred nanometers). Moreover, the use of donor and acceptor beads can generate autofluorescence in tissue. Autofluorescence is typically observed as emission of light across a relatively wide band of visible wavelengths. Autofluorescence functions as a background signal against which fluorescence emission signals from acceptor beads that indicate the presence of ROS are distinguished.

The present disclosure features compositions of particles for detecting and imaging ROS in-vivo that do not include both donor and acceptor beads. Instead, particles in the compositions disclosed herein feature targeting groups that bind to structural entities in the subject's body, reacting groups that react with ROS to generate radiation, and luminescent agents that absorb the generated radiation and emit luminescence. The luminescence can be detected (e.g., imaged) to show spatial location and quantification of the ROS in the subject's body.

For purposes of this disclosure, reactive oxygen species (ROS) include single oxygen, hydroxide radical, hypochlorous acid, superoxide radical, nitric oxide, hydrogen peroxide, and other products of mediation by oxidases such as myeloperoxidase and horseradish peroxidase.

Figure 1:
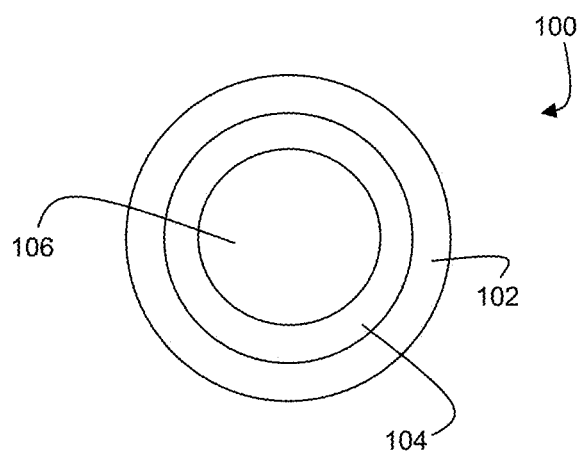
FIG. 1 is a schematic diagram of a particle for in-vivo detection of reactive species.

FIG. 1 is a schematic diagram of a particle 100 that includes a core 102, a first coating material 104, and a second coating material 106. Particle 100 reacts with ROS in a subject's body and emits luminescence. Core 102 typically corresponds to a bead formed of one or more biologically compatible materials. In some embodiments, for example, core 102 can be formed of latex, polystyrene, acrylic acid, amides, and other materials bearing unsaturated groups such as olefinic and/or acetylenic groups that can be polymerized, e.g., under emulsive conditions.

First coating material 104 and second coating material 106 typically each include one or more polysaccharides. In general, a wide variety of different polysaccharides can be used alone or in combination to form coating materials 104 and 106. For purposes of this disclosure, suitable polysaccharides that can be used to form coating materials 104 and 106 include, carbohydrates that include three or more non-modified or modified monosaccharide units, such as, e.g., dextran, starch, glycogen, inulin, levan, mannan, agarose, galactan, carboxydextran and/or aminodextran. Examples of polysaccharides include, but are not limited to, dextran, starch, glycogen, polyribose, and functionalized derivatives thereof.

Core 102 also includes at least one reacting group that reacts with one or more ROS to generate radiation. In general, a variety of different materials can be used as reacting groups in core 102. Examples of suitable reacting groups include thioxene derivatives, electron rich olefins in dioxetanes, dienes, and aromatics, either as isolated species or conjugated with an acceptor dye moiety. Reacting groups are further disclosed in the following U.S. Patents, the entire contents of each of which is incorporated herein by reference: U.S. Pat. Nos. 6,406,913; 6,692,975; 6,916,667; and 6,406,667.

Core 102 also includes at least one luminescent agent. The at least one luminescent agent absorbs radiation emitted by the reacting groups, and emits luminescence. Typically, the central wavelength of the emitted luminescence is larger than the central wavelength of the absorbed radiation, where the central wavelength refers to the center of the full-width at half-maximum of the distribution of the absorbed or emitted radiation. For example, in some embodiments, the central wavelength of the emitted luminescence is 500 nm or more (e.g., 550 nm or more, 600 nm or more, 650 nm or more, 700 nm or more, 750 nm or more, 800 nm or more, 850 nm or more).

A variety of different luminescent agents can be used in core 102. In some embodiments, for example, the luminescent agents can include one or more lanthanide elements (e.g., one or more of lanthanum, cerium, praseodymium, neodymium, promethium, samarium, europium, gadolinium, terbium, dysprosium, holmium, erbium, thulium, ytterbium, and lutetium). Among these elements, europium and terbium are particularly advantageous for use as luminescent agents.

Second coating material 106 includes at least one targeting group that binds to a structural entity in the subject. Structural entities in the subject typically include proteins, antibodies, nucleic acids, aptamers, truncated forms of antibodies such as Fabs, cysbodies, and diabodies, and other chemical structural moieties that are of interest. Structural entities that are targeted by the at least one targeting group include, but are not limited to, poly(amino acids), i.e., polypeptides and proteins, polysaccharides, nucleic acids, and combinations thereof. Such combinations include components cells, such as chromosomes, genes, mitochondria, nuclei, and cell membranes. In general, the poly(amino acids) have a molecular weight of between 5,000 and 5,000,000 Daltons. Structural entities can also include oligonucleotides and polynucleotides such as m-RNA, r-RNA, t-RNA, DNA (double stranded ("ds") or single stranded ("ss")), RNA (ds or ss), DNA-RNA duplexes, etc. An "oligonucleotide" is a single stranded polynucleotide including a synthetic polynucleotide. Oligonucleotides typically include a sequence of 10 to 100 nucleotides. A "polynucleotide" is a compound or composition which is a polymeric nucleotide having in the natural state about 50 to 500,000 or more nucleotides. Polynucleotides include nucleic acids from any source, such as DNA (dsDNA and ssDNA) and RNA (dsRNA and ssRNA), t-RNA, m-RNA, r-RNA, mitochondrial DNA and RNA, chloroplast DNA and RNA, DNA-RNA hybrids and/or mixtures thereof, genes, chromosomes, plasmids, and genomes of biological material.

Targeting groups that bind to the structural entities include groups that include a structural feature or region that specifically binds to, and is therefore complementary with, one or more of the structural entities in the subject. A variety of different targeting groups can be present in second coating material 106, including one or more naturally occurring and/or synthetic molecules, e.g., thyroxine binding globulin, steroid-binding proteins, antibodies, Fab fragments or other antigen-binding fragments of antibodies, enzymes, lectins, nucleic acids, repressors, oligonucleotides, protein A, protein G, avidin, streptavidin, biotin, complement component C1q, DNA binding proteins, and RNA binding proteins. The targeting groups can be members (together with the structural entities in the subject) of an immunological pair such as antigen-antibody or haptenantibody, operator-repressor, nuclease-nucleotide, biotin-avidin, lectin-polysaccharide, steroid-steroid binding protein, drug-drug-receptor, hormone-hormone receptor, enzyme-substrate, IgG-protein A, and/or oligo- or polynucleotide-complementary oligo- or polynucleotide.

In general, one of first coating material 104 and second coating material 106 includes amine functional groups, and the other coating material includes amine-reactive functional groups. For example, the polysaccharide(s) of first coating material 104 can be covalently coupled to core 102 by reaction between amine-reactive functional groups of the core (i.e. carboxyl groups) and amine groups of the polysaccharide(s). The polysaccharide(s) of second coating material 106 can be covalently coupled to the polysaccharides of first coating material 104 by reaction between the amine functional groups of the polysaccharide(s) of the first coating material 104 and amine-reactive functional groups of the polysaccharide(s) of second coating material 106. Conversely, in some embodiments, core 102 has amine functional groups that react with amine-reactive functional groups of the polysaccharide(s) of first coating material 104. The polysaccharide(s) of second coating material 106 also include amine-reactive functional groups.

Particle 100 in FIG. 1 includes two coating materials 104 and 106. More generally, however, more than two coating materials can be used. In some embodiments, for example, one or more additional coating materials can be applied to particle 100. The additional coating materials can generally include any of the materials disclosed herein in connection with coating materials 104 and 106. For example, the additional coating materials can each include one or more polysaccharides.

Additional coating materials can also include any one or more of the additional components disclosed herein. For example, in some embodiments, additional coating materials can include one or more additional targeting groups that bind to specific structural entities within the subject. The targeting groups can include any of the targeting groups disclosed above. Providing additional targeting groups, either in second coating material 106 or in additional coating materials, can allow particle 100 to bind to a wide variety of structural entities.

As an example, the following describes a preparative method for a plurality of particles 100 that include a first coating material 104 featuring aminodextran (AmDex) and a second coating material featuring dextran aldehyde (DexAl), with specific reactive groups and luminescent agents. However, it should be understood that this method is merely illustrative of only certain embodiments, and can readily be adapted to include any of the first and second coating materials, reactive groups, luminescent agents, and targeting groups disclosed herein.

Figure 10:
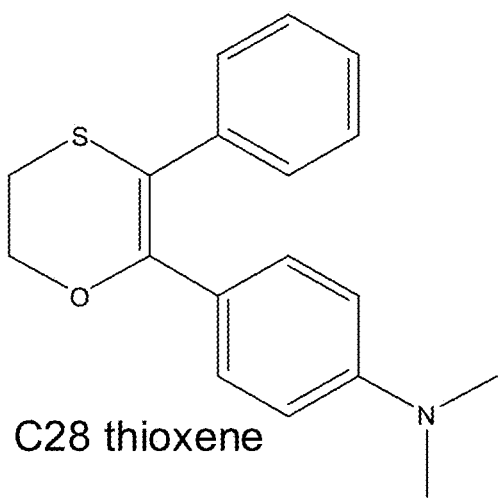
FIG. 10 is a schematic diagram of the chemical structure of C-28 thioxene dye.

Carboxylated latex or polystyrene particles were obtained in their native, uncoated state. To introduce the reacting group(s) and luminescent agent(s), the particles were heated to slightly below their glass transition temperature, rendering them porous. A quantity of thioxene dye (C-28 thioxene, shown in FIG. 10), which functions as the reacting groups, was added to the beads. Further, chelated europium and/or terbium was added to the beads (structure shown in FIG. 11, with La=Eu, Tb). The particles had a diameter of between 190 nm and 210 nm, and a surface carboxy-group concentration of about 60,000 per particle.

To introduce C-28 thioxene and chelated Eu or Tb, 5 mL Seradyn carboxylated polystyrene particles (diameter~200 nm) at a concentration of 100 mg/mL were added to a 50 mL flask, along with 75 μL NaOH at 1 M, 7.0 mL 2-ethoxyethanol, and 20.5 mL water. The particle suspension was heated to 80° C. using an oil bath with constant stirring. To a glass vial were added 100 mg C-28 thioxene, 135 mg chelated Eu or Tb (e.g., $Tb(XTA)_3 \cdot Phen$), and 11 mL 2-ethoxyethanol. This solution was added to the stirred particle suspension at 80° C. Heating and stirring continued for another 25 minutes. The mixture was then cooled to room temperature with continued stirring.

The suspension was filtered, and 200 mL EtOH 10% at pH>10 was added to the filtrate and mixed. The combined suspension was centrifuged for 20 minutes at 15,000 rcf using an Eppendorf 5417C centrifuge. After centrifugation, the liquid was decanted and the particles re-suspended in 10% EtOH at pH>10, and briefly sonicated.

Chelated Eu and/or Tb was prepared in a one-step synthesis. The procedure below discloses the preparation of chelated Tb, but can also be used for chelated Eu with minor modifications. 3.72 grams (10 mmol) of $TbCl_3 \cdot 6H_2O$ in 30 mL water were added to a 250 mL Erlenmeyer flask. 90 mL of absolute EtOH was added to the solution and mixed to achieve a homogeneous distribution. Next, 6.48 g (30 mmol) of 1-benzoyl-3,3,3-trifluoroacetonate (BTA) was added to the solution with stirring for 1 hour to complete dissolution. Then, 6.6 mL of 5 M NaOH (33 mmol) was added slowly, maintaining the pH between 6 and 7. The solution was heated to between 50° and 60° C. for 1 hour with stirring.

Meanwhile, 1.80 g (10 mmol) of 1,10-phenanthroline was dissolved in 30 mL absolute EtOH, and was added to the still-warm solution following heating. The combined solution was stirred for 1 hour without further heating, forming a precipitate. The mixture was allowed to cool during stirring. Stirring continued at high speed to prevent clumping of the product. 150 mL of water was added to the mixture, which was then mixed thoroughly for another hour. The slurry was then cooled for 1 hour in a refrigerator at about 4° C. Solids were filtered from the mixture using a Buchner funnel, and were washed 3 times with 50 mL water. The solid chelated Tb product was transferred to a Petri dish and allowed to air dry for several days at room temperature, or dried in a vacuum dessicator overnight.

Figure 11:
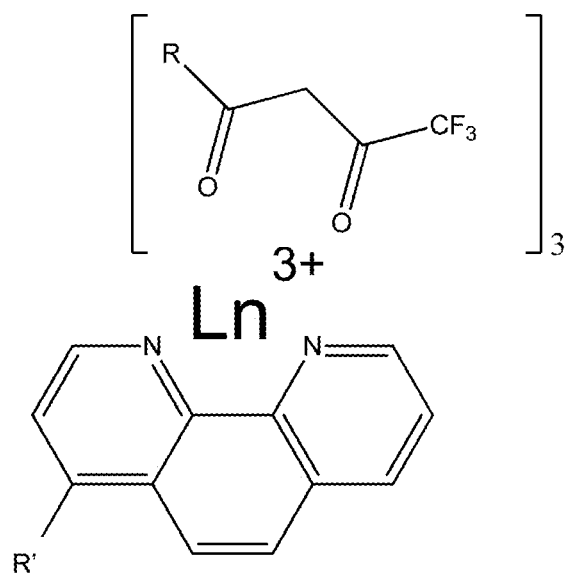
FIG. 11 is a schematic diagram of the chemical structure of a chelated lanthanide element such as europium or terbium.
Figure 12:
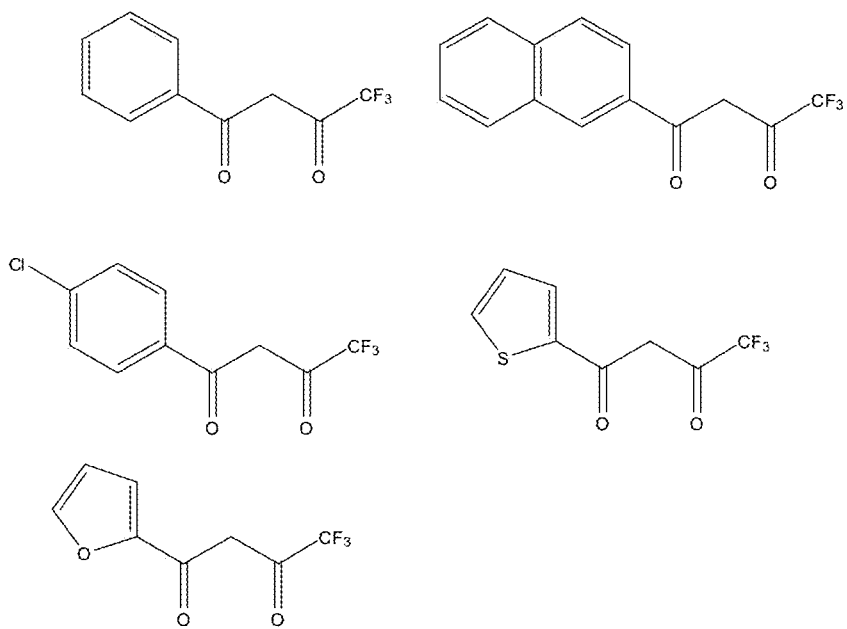
FIG. 12 is a schematic diagram of the chemical structures of examples of di-ketonate ligands that can be used to chelate lanthanide elements.
Figure 13:
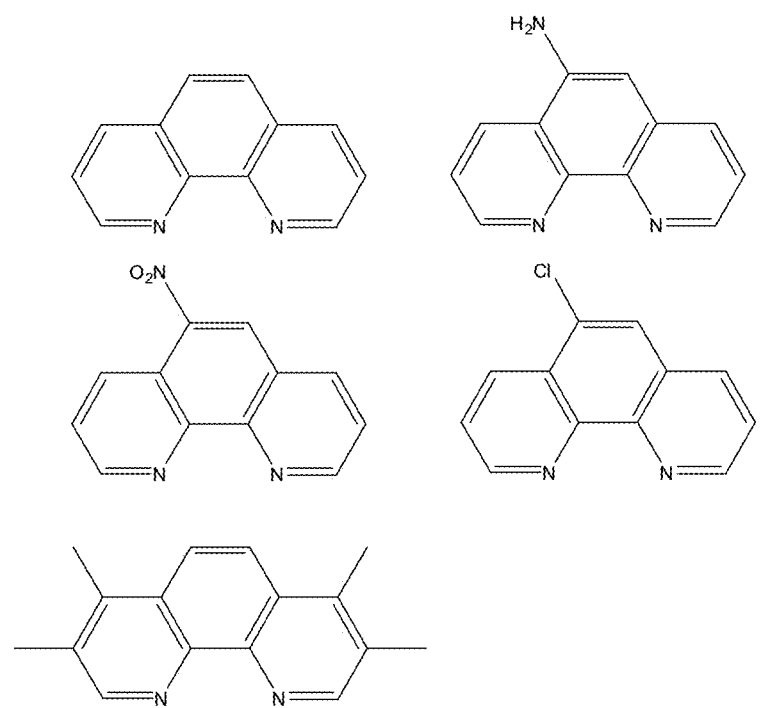
FIG. 13 is a schematic diagram of the chemical structures of examples of phenanthroline ligands that can be used to chelate lanthanide elements.

In general, a variety of different diketonates can be used in the procedure described above (e.g., with different substituents corresponding to aromatic ring R in FIG. 11). Examples of suitable diketonates are shown in FIG. 12. Further, a variety of different phenanthrolines can be used in the procedure described above (e.g., with different substituents corresponding to group R'). Examples of suitable phenanthrolines are shown in FIG. 13.

The preparation of suitable thioxene dyes and chelated lanthanide elements, including chelated europium and terbium, is also described for example in the following patents, the contents of each of which is incorporated by reference herein: U.S. Pat. Nos. 5,340,716; 6,251,581; 6,406,913; 6,692,975; 6,916,667; 7,179,660.

Next, the particles (i.e., cores 102 with reacting groups and luminescent agents added) were coated with AmDex molecules (having multiple amino groups per AmDex molecule) using carbodiimide (EDAC) conjugation chemistry. The presence of opposite charges on the particle surface ($—COO^-$) and on the AmDex ($—N^+H_3$) attract each other and in the presence of a relatively large excess of AmDex, the particle surface is rapidly and effectively covered by AmDex molecules, even in the absence of EDAC. In this fashion, the polysaccharide spontaneously associates with the particles, leading to an increased concentration of amino groups near to the surface of the particles which in turn improves the efficiency of the EDAC conjugation method. Adding EDAC at this point activates the —COOH groups on the particle, which subsequently react with —$NH_2$ groups on AmDex leading to the formation of a chemically stable amide bond. Only a fraction of the amino groups from the AmDex molecule are involved in forming the covalent amide bond and the remaining amino groups are available for reactions with various other groups (e.g., aldehyde groups or carboxyl groups). The coated particles had a diameter of between 240 nm and 270 nm, with 1 amino group for every 12 saccharides.

To coat the particles, 300 mg of particles in suspension were spun down and the liquid removed. The particles were re-suspended in 100 mM 2-(N-morpholino)ethanesulfonic acid (MES) at pH 6.0 to a concentration of 20 mg/L, for a total volume of 15 mL. To this suspension was added 15 mL of amino-dextran at a concentration of 8 mg/mL in water, 5 mL EDAC at a concentration of 80 mg/mL in water. After mixing, the mixture was incubated for 2 hours at room temperature with agitation. The particles were then washed twice with 100 mM MES at pH 6.0 by centrifugation at 15,000 rcf for 20 minutes. The particles were washed once with 0.1 N HCl and finally collected in 12.5 mL of 100 mM MES at pH 6.0 and sonicated.

The particles were subsequently coated with a second polysaccharide layer by reacting the particles with a relatively large excess of dextran aldehyde (DexAl) having multiple aldehyde groups per DexAl molecule. This spontaneous reaction is a form of spontaneous association of the polysaccharide layers. A fraction of the aldehyde groups on a DexAl molecule react with amino groups on the AmDex layer forming shiff-base, which then can be reduced with a mild reducing agent such as cyanoborohydride ($NaBH_3CN$) to form a chemically stable carbon-nitrogen bond. Since the reduction of free aldehyde groups by $NaBH_3CN$ is negligible, the resulting coated particles have reactive aldehyde groups on the surface and can react with amino group containing molecules (such as antibodies or other proteins or further AmDex molecules). The coated particles had a diameter of 260 nm to 310 nm, with 1 aldehyde group for every 16 saccharides (approximately 30,000 to 50,000 per particle).

To apply the second polysaccharide layer, 5 mL of the particle suspension (concentration 20 mg/mL) was added to a glass vial, along with 0.8 mL dextran aldehyde solution (concentration 50 mg/mL), 4.2 mL of 0.1 M MES at pH 6.0, and 0.5 mL NaBH$_3$CN at a concentration of 80 mg/mL in water (freshly prepared). After mixing, the vial was closed with a screw cap and incubated at 37° C. overnight. After equilibrating to room temperature, the particles were washed twice with 0.1 M MES at pH 6.0 by centrifugation at 15,000 rcf for 20 minutes. The particles were then sonicated and collected in approximately 4 mL of 0.1 M MES at pH 6.0.

One or more targeting groups were then conjugated to the second polysaccharide layer. The conjugation was performed by a reductive amination method, in which purified antibody in native form (not modified) was incubated with the particles in presence of NaBH$_3$CN for a certain period of time, preferably at room temperature or at 37° C. The remaining free aldehyde groups were capped (various molecules can be used for this purpose, for example carboxymethyl oxime or carboxymethoxylamine, etc.)

Conjugation typically occurs best when the antibody concentration is at least 1 mg/mL (for conjugation of 1-2 mg of particles) or 0.53 mg/mL (for conjugation of 2.5 mg or more of particles). Antibody solutions can be concentrated, for example, using an iCON Concentrator (available from ThermoFisher Scientific, Waltham, Mass.). Typically, the antibodies are not in an amine-based buffer (e.g., Tris, glycine, bicine, tricine). If buffer exchange is undertaken, the buffer solution is generally replaced by a neutral or slightly alkaline buffer such as PBS or carbonate buffer at a pH of about 8.0. In addition, antibody solutions used for conjugation typically do not include protein- or peptide-based stabilizers (e.g., BSA, gelatin) or glycerol. Protein stabilizers can be removed using PhyTip affinity columns (available from PhyNexus, San Jose, Calif.) or a liquid handling system such as the JANUS automated workstation (available from PerkinElmer, Waltham, Mass.). Dialysis can be used to remove glycerol.

When conjugating particles, the ratio of antibody to mass of particles is an important parameter. Typical coupling ratios (e.g., mass of particles to mass of antibody) are either 10:1 (for 1-2 mg of particles) or 50:1 (for 2.5 mg of particles or more). For example, for 5 mg of particles, 0.1 mg of antibody is typically used.

The following procedure was used to conjugate 5 mg of particles, using a 50:1 coupling ratio with an antibody. The antibody solution used typically has a concentration of 0.53 mg/mL or more. The particles were first washed in a 1.5 mL Eppendorf tube in 250 µL of water, and then 250 µL of PBS was added. The suspension was centrifuged at 16,000 g (or maximum speed) for 15 minutes and the supernatant liquid discarded using a pipet tip.

A fresh working solution of NaBH$_3$CN (obtained in powder form from Sigma-Aldrich, St. Louis, Mo.) at a concentration of 400 mM in water was prepared by adding 25 mg of NaBH$_3$CN powder to 1 mL of water. To the Eppendorf tube containing the washed particles were added 0.1 mg of antibody, a volume of 100 mM Hepes pH 7.4, to achieve a final reaction volume of 200 µL, 1.25 µL of 10% Tween-20 (obtained from Thermo-Fisher Scientific), and 10 of the aqueous NaBH$_3$CN solution. The suspension was incubated for 18-24 hours at 37° C. using a rotary shaker at 6-10 RPM.

Next, a fresh 65 mg/mL solution of carboxymethoxylamine (CMO) (obtained from Sigma-Aldrich) in 800 mM NaOH was prepared, and 10 µL of the CMO solution was added to the suspension, which was incubated for an additional 1 hour at 37° C. using a rotary shaker at 6-10 RPM. The CMO solution blocks unreacted sites on the particles.

The conjugated particles were then washed. First, the particles were centrifuged for 15 minutes at 16,000 g (or maximum speed) at 4° C. The supernatant was removed using a micropipette and the dehydrated particle pellet was resuspended in 1 mL of 100 mM Tris-HCl pH 8.0 (using about 200 µL per mg of particles). The particle suspension was briefly sonicated (10 short pulses of 1 second using a probe sonicator) to ensure the particles were not aggregated at a sonicator power of approximately 20% or maximum power. The suspension was then centrifuged for 15 minutes at 16,000 g or maximum speed at 4° C., and the supernatant removed.

The foregoing washing steps were then repeated. Following the last centrifugation, the particles were re-suspended at a concentration of 5 mg/mL in a storage buffer (1 mL of PBS and 0.05% Proclin-300 as a preservative). The suspension was vortexed, briefly spun down, and sonicated using 10 short pulses of 1 second using about 20% of maximum sonication power.

Conjugated particles were stored in opaque vials at a temperature of 4° C. Prior to use, the suspensions were vortexed again to counteract settling during storage.

To conjugate quantities of particles larger than 5 mg, the foregoing procedure was adapted to use a 50 mL 3118 Oak Ridge centrifuge (available from Thermo Fisher Scientific) with a maximum volume in each tube of less than about 30 mL to allow proper centrifugation. Centrifugation steps were performed in a Sorvall RC-5B centrifuge (Thermo Fisher Scientific) at 16,000 g for 40 minutes at 4° C.

In general, the particle coupling procedure disclosed herein can be optimized (e.g., to increase the number of antibodies bound per particle) by reducing the reaction volume, as coupling efficiency typically increases with particle concentration. Increased particle concentrations, up to 100 mg/mL, can be prepared by adding a smaller volume of a more concentrated buffer solution to the particles.

The procedure can also be optimized by increasing the ratio of antibody to particles, as coupling efficiency typically increases with antibody concentration. In general, the antibody stock solution should be sufficiently concentrated so that only a small additional volume of the antibody solution is added to increase the antibody concentration without significantly diluting the particle concentration. For example, a 10:1 ratio of particles:antibody, when implemented at a particle concentration of 25 mg/mL, can improve conjugation efficiency. Increasing the particle concentration to 75 mg/mL while maintaining a ratio of 50:1 will typically involve an antibody concentration of 1.7 mg/mL. Increasing the relative proportion of antibody to a ratio of 25:1 will involve an antibody concentration of 3.4 mg/mL, which is close to the practical upper limit. Other buffers can also be used to optimize the foregoing procedure (e.g., 100 mM sodium phosphate at pH 8.0).

Additional preparative methods and materials are disclosed, for example, in the following patents and patent publications, the entire contents of each of which is incorporated herein by reference: U.S. Pat. Nos. 5,340,716;

6,251,581; 6,406,913; 6,692,975; 6,916,667; 7,179,660; and PCT Patent Publication No. WO 2001/067105.

The particles disclosed herein can be introduced into a living subject using a variety of methods, including injection, e.g., subcutaneous injection, intravenously, intratracheally, intranasally). Typically, the particles are introduced in proximity to a region of interest in the subject, e.g., near the site of a suspected tumor or tissue inflammation. The targeting groups are selected so that the particles bind selectively to certain structural entities, e.g., entities that are present in the region of interest. The targeting of specific structural entities within the subject allows the particles to function as sensitive diagnostic reporters for reactive species, e.g., reactive oxygen species in the subject's body.

The particles can be used detect and image reactive species such as ROS in a variety of different subjects. In general, the particles can be used for in-vivo detection and imaging in humans, in mammals (including, but not limited to, mice, rats, dogs, and cats, and more generally, any laboratory mammalian subject), in birds, reptiles, amphibians, and fish. The particles can also be used for in-vitro detection and imaging of tissue samples and/or biological fluids extracted from any of the foregoing subjects.

After introducing the particles into the subject's body, luminescence emitted by the particles is imaged using a detector (e.g., a CCD-based detector or a CMOS-based detector). In combination with light reflected from the surface of the subject, the emitted luminescence shows where reactive species, such as reactive oxygen species, are located within the subject's body. In some embodiments, the detected luminescence can be displayed directly to a viewer without filtering the luminescence. In certain embodiments, the detected luminescence can be overlaid on an image of the subject's body. Both of these display modalities can yield images that localize the ROS relative to other features of the subject's body.

The intensity and distribution of luminescence detected can also provide quantitative information about ROS in the subject's body. For example, by spatially integrating portions of the luminescence image of the subject and correlating the integrated intensity with calibration data that relates light intensity to ROS concentration, the concentration of ROS in the integrated region of the subject's body can be estimated. Quantitative estimates of ROS concentrations can provide additional information for purposes of diagnosing diseases in the subject.

In some embodiments, more than one type of particle can be administered to the subject. For example, the plurality of particles that is administered can include a first subset of particles with one type of targeting group and a second subset of particles with a second type of targeting group. By providing particles with different targeting groups, the particles can bind to different structural entities within the subject, thereby providing diagnostic ROS information about multiple regions of the subject's body.

Additionally, or alternatively, the first subset of particles can include a first luminescent agent and the second subject of particles can include a second luminescent agent. Different luminescent agents typically emit luminescence at different central wavelengths. Thus, subsets of particles with different luminescent agents can be used to provide information about different regions of a subject's body.

For example, in some embodiments, the first subset of particles can include both targeting groups and luminescent agents that are different from the targeting groups and luminescent agents of the second subset of particles. Providing subsets of particles with these features yields two-fold selectivity in targeting particular structures or regions within a subject's body. First, the two subsets of particles bind to different structural entities in the subject on account of their different targeting groups, thereby providing a first mechanism for distinguishing the different entities. Second, luminescence from the different subsets of particles occurs at different central wavelengths. Accordingly, by filtering and/or selectively detecting luminescence at certain wavelengths, ROS in the different structural entities can be separately identified and quantified.

Figure 2:
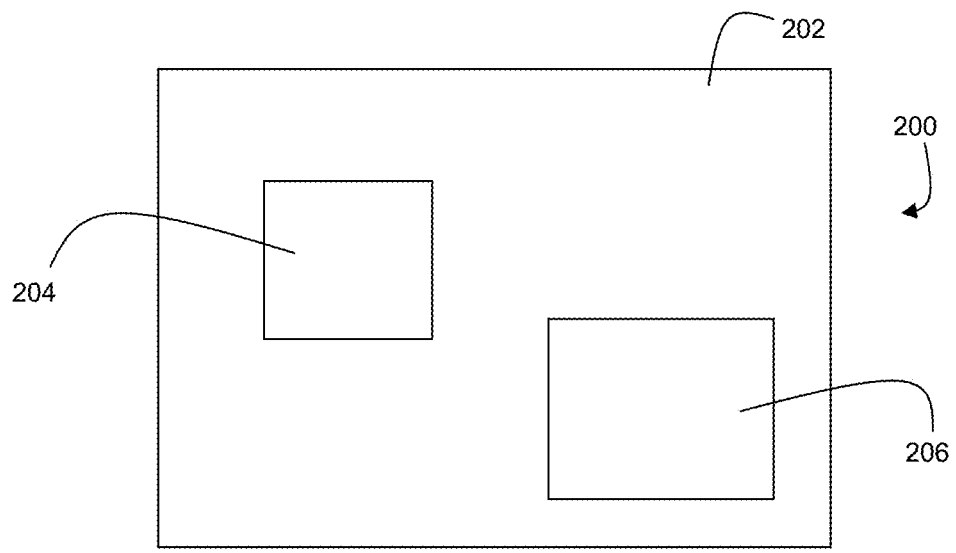
FIG. 2 is a schematic diagram of a kit that includes particles for in-vivo detection of reactive species.

The particles disclosed herein can be provided in a diagnostic kit for clinical use. FIG. 2 is a schematic diagram of a kit 200 that includes a housing (e.g., a wrapper) 202. Enclosed within the housing is a container 204 that includes a plurality of particles 100. Optionally, kit 200 can include a second container 206 that includes, for example, one or more buffer solutions for introducing the particles into a subject's body (e.g., via injection). In some embodiments, particles 100 are provided in container 204 in an unsuspended (e.g., dry) form. Prior to administering the particles, the particles are suspended in a solution provided in second container 206. In certain embodiments, particles 100 are provided in container 204 already suspended in a physiologically-compatible solution. The particles can either be administered directly to the subject, or diluted to a desired concentration (e.g., in a buffer or other solution) before they are administered to the subject.

The particles disclosed herein provide a number of important advantages. For example, the particles emit luminescence, which is detected and used to localize and quantify ROS in the subject. In contrast to fluorescence, luminescence typically occurs toward the red edge of the visible region of the spectrum, and in the near-infrared region. As a result, particles which emit luminescence are better suited to act as reporters for ROS in deep tissue applications (e.g., where ROS are located in tissues more than about 2 mm below the skin surface) because tissue-dependent scattering of radiation is not as strong at longer wavelengths. Thus, the particles disclosed herein provided significantly improved diagnostic sensitivity for ROS located in deep tissues relative to fluorescence-based particles and reporters.

In addition, fluorescence-based reporters are typically accompanied by autofluorescence in the subject's tissue, which functions as a background signal against which fluorescence emission due to detection of ROS is distinguished. In contrast, the luminescence-based particles disclosed herein do not typically excite, and are not typically accompanied by, significant autofluorescence in the subject's tissue. As a result, the luminescence emission typically occurs against an essentially "dark" background; removal of autofluorescence contributions (e.g., by sophisticated analysis algorithms) is generally not required. In some embodiments, for example, the detected luminescence can be used to visualize and quantify ROS in the subject's body without any filtering of the signal measured by the detector.

Further, the particles disclosed combine selective binding, reaction with ROS, and luminescent reporting of ROS in a single particle. Conventional two-particle methods for detecting ROS, which involve both donor and acceptor particles, provide acceptable signals only when donor and acceptor particles approach one another closely enough. In contrast, the particles disclosed herein do not rely on the distance between particles to detect ROS. Instead, each particle includes a reacting group that reacts with ROS, and a luminescent agent that emits luminescence in response to energy transfer from the reacting group. Because the luminescent agent and reacting group are located on the same particle, the energy transfer is efficient.

Although the methods and compositions disclosed above are directed to particles for detection of reactive oxygen species in vivo, more generally the methods and compositions can also be applied to the detection of other reactive species in vivo. For example, the methods and compositions can be applied to in vivo detection of reactive nitrogen species (e.g., NO, NO radical, and peroxynitrite anion ONOO$^-$). To detect reactive nitrogen species, particles 100 can include one or more reacting groups that react with reactive nitrogen species, emitting radiation that is absorbed by the luminescent agent(s) to cause luminescence emission. Suitable reacting groups include, for example DAF-FM (available from Thermo Fisher Scientific), which is a reagent that is used to detect and quantify low concentrations of nitric oxide (NO). DAF-FM is essentially non-fluorescent until it reacts with NO to form a fluorescent benzotriazole. DAF-FM fluorescence can be detected using a variety of different techniques and devices, including flow cytometers, microscopes, fluorescent microplate readers and fluorometers, and imaging systems such as the IVIS and FMT systems, available from from Perkin Elmer.

Additional reacting groups and substrates therefor are disclosed, for example, in Xiaoqiang Chen et al., "Fluorescent and luminescent probes for detection of reactive oxygen and nitrogen species," *Chem. Soc. Rev.* 40: 4783-4804 (2011), the entire contents of which are incorporated herein by reference.

EXAMPLES

The subject matter disclosed herein is further described in the following examples, which are not intended to limit the scope of the claims.

To evaluate the efficiency with which various ROS are detected using the particles disclosed herein, quantities of HOCl, hydroxide radical, superoxide, nitric oxide, and hydrogen peroxide were prepared in vitro. Each of these in vitro species was treated with particles 100, which were prepared as described above and included latex cores, a first coating of aminodextran, and a second coating of dextran aldehyde. A thioxene dye and chelated europium were introduced into the latex cores before coating.

Figure 3:
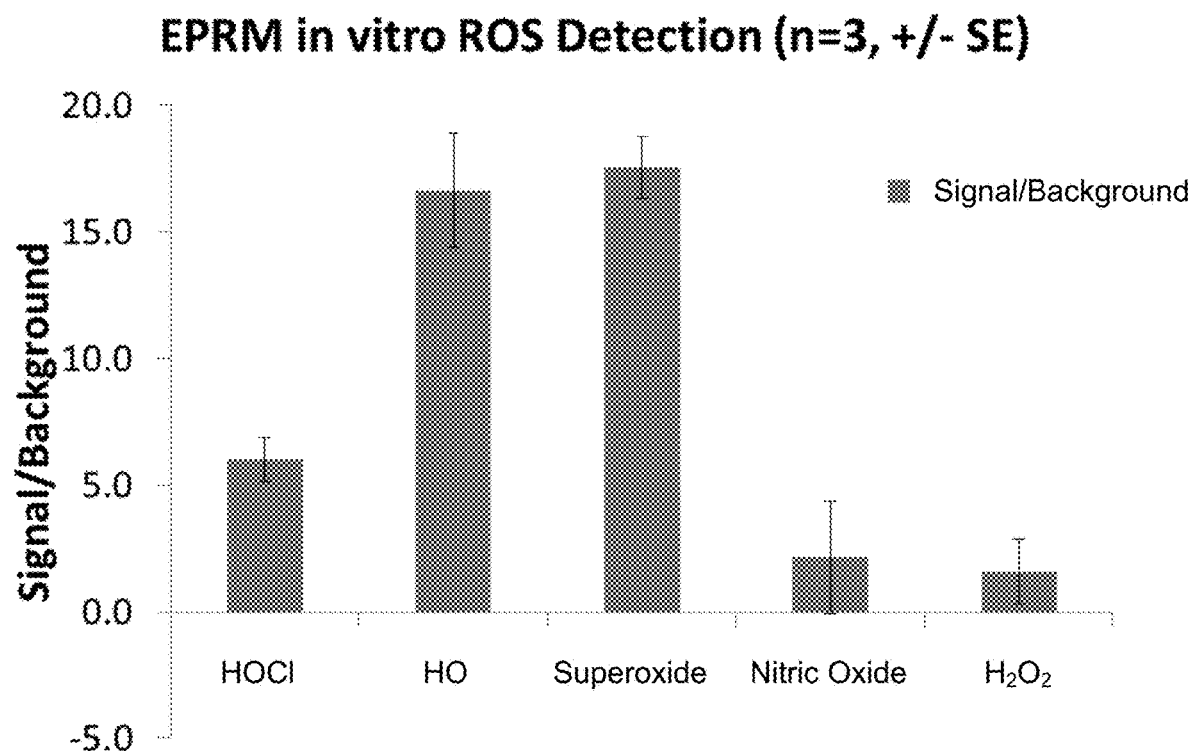
FIG. 3 is a graph showing luminescence signals for reactive oxygen species detected in vitro by a plurality of particles.

FIG. 3 is a graph showing a comparison of luminescence signal/background detected for each of the different ROS. Each of the species was reliably detected, with hydroxyl radical and superoxide having the highest signal above background.

Figure 4:
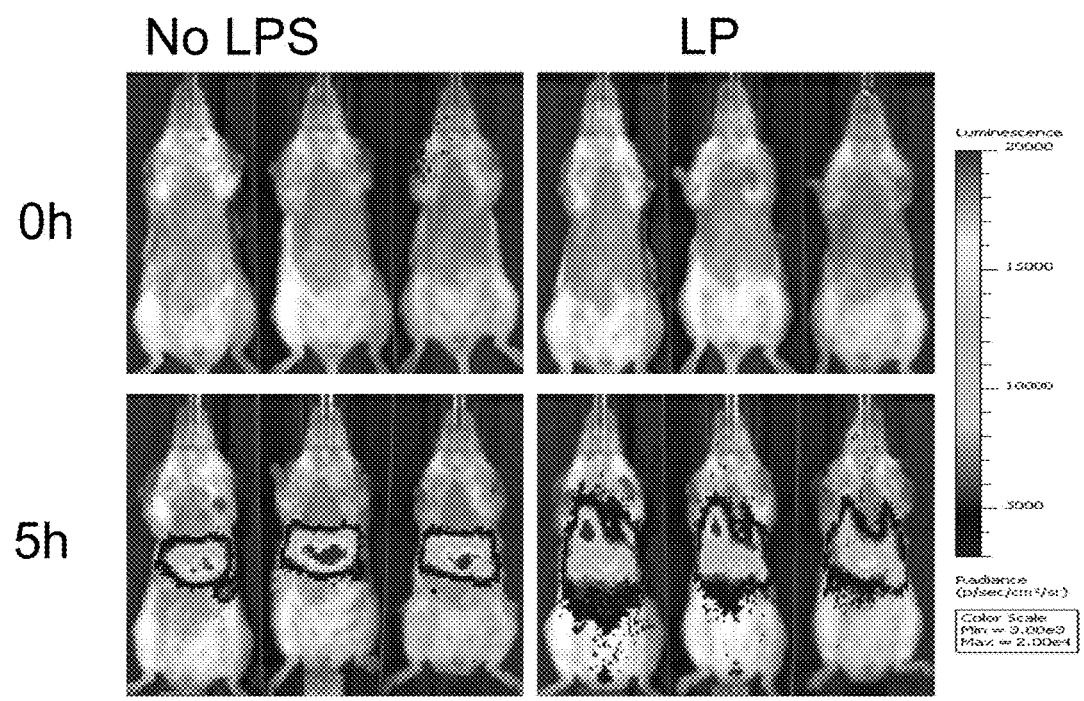
FIG. 4 is a series of images showing measured luminescence signals corresponding to reactive oxygen species in two groups of murine subjects.

To evaluate the efficiency of in vivo murine detection of ROS, a sample of BALB/cJ mice subjects were divided into two groups. The first group was challenged by intracheal delivery of 50 µL of 1 mg/kg lipopolysaccharide (LPS) at a concentration of 1 mg/kg i.n. to induce an inflammatory response. The second group, functioning as the control, was challenged with phosphate buffered saline (PBS). A 10 µg quantity of particles (prepared as described above, with aminodextran and dextra aldehyde coatings, thioxene dye and chelated europium introduced into the latex core) were introduced into both lung and liver sites via subcutaneous injection 3 hours after the LPS challenge. Luminescence emission from the injected particles was imaged as a function of time following the injection of the particles. FIG. 4 shows images of control (left side) and LPS-challenged (right side) subjects immediately following the injection, and after a period of 5 hours.

Figure 5A:
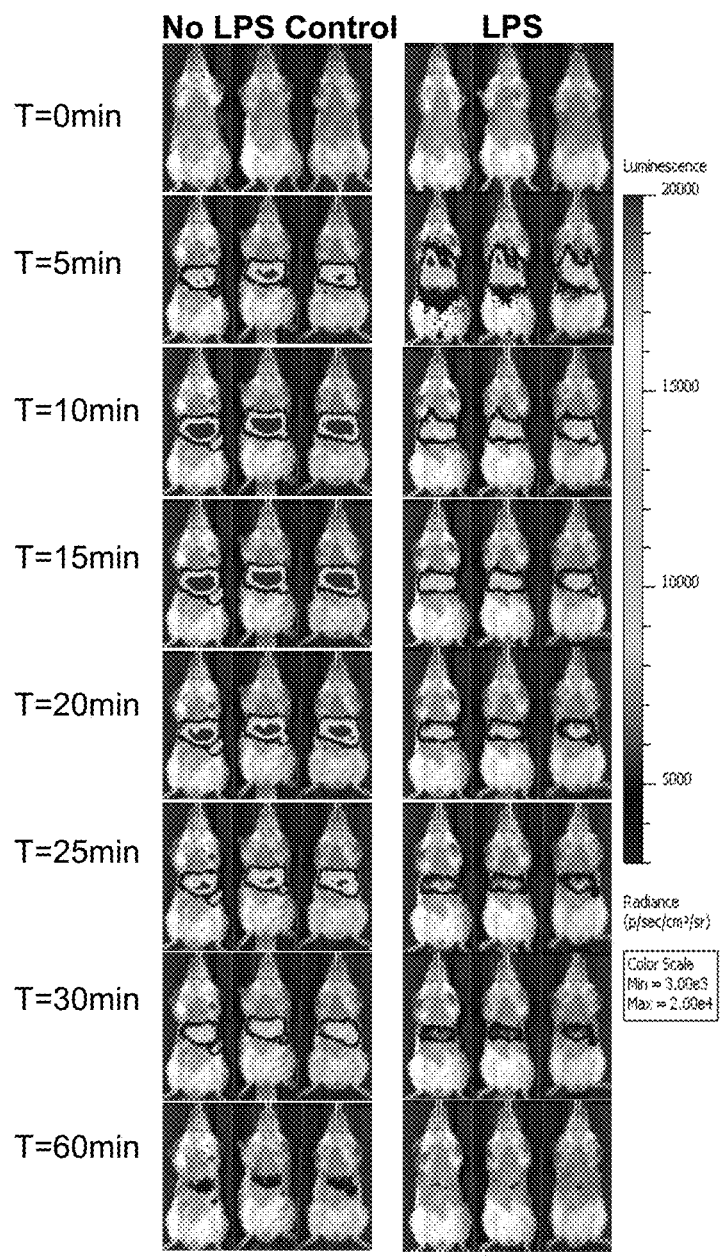
FIG. 5A is a series of images showing measured luminescence signals from the same murine subjects as in FIG. 4, obtained over a period of 1 hour.
Figure 5B:
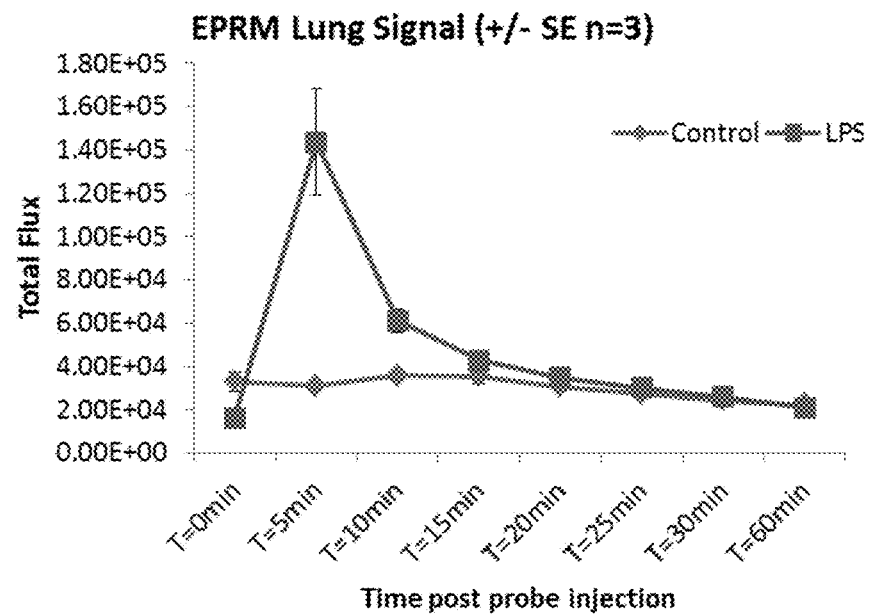
FIG. 5B is a graph showing luminescence signals measured from lung tissue for the same murine subjects as in FIG. 4.
Figure 5C:
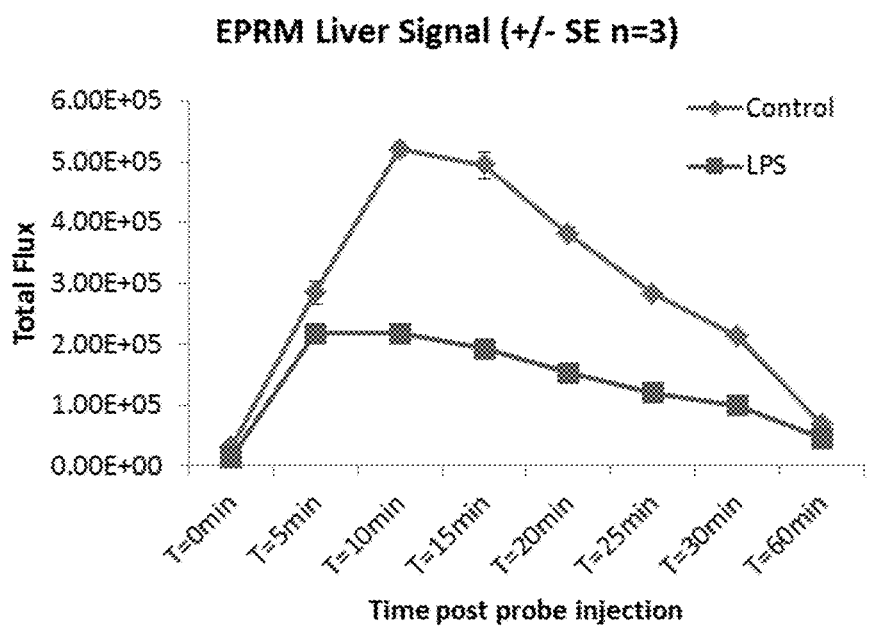
FIG. 5C is a graph showing luminescence signals measured from liver tissue for the same murine subjects as in FIG. 4.

FIG. 5A shows images of control (left side) and LPS-challenged (right side) subjects in 5 minute increments in the first hour following injection of the particles. FIGS. 5B and 5C show measured luminescence fluxes (arbitrary units) from both lung and liver tissues as a function of time, determined from the images in FIG. 5A. Measured luminescence from the lung tissue demonstrated that ROS were efficiently detected compared to the background signal corresponding to the control. Luminescence signals from liver tissue showed high background levels of luminescence due to the presence in the liver of cytochrome P450 oxidoreductases, which generate ROS.

To improve the selective targeting of lung tissues by the particles, particles were prepared as described above (e.g., with aminodextran and dextra aldehyde coatings, thioxene dye and chelated europium introduced into the latex core) and conjugated to Ly6G antibodies, which bind to lung tissues. One group of BALB/cJ mice subjects was challenged with LPS intranasally with five 25 µL doses of 0.25 mg/mL LPS, followed by 25 µL of PBS. A control group of mice was challenged intranasally with five 25 µL doses of PBS. Both groups of mice were allowed to wake up between doses. Five hours after the initial challenge, the mice were injected with the Ly6G-conjugated particles, and luminescence emission from the particles was imaged.

Figure 6A:
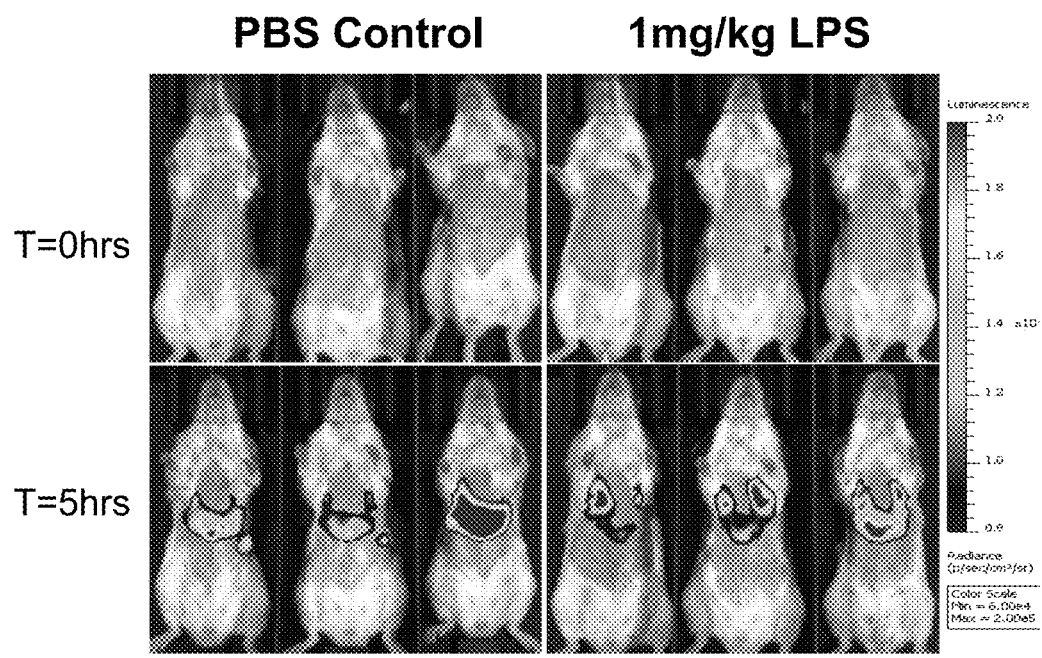
FIG. 6A is a series of images showing measured luminescence signals from antibody-conjugated particles in two groups of murine subjects.
Figure 6B:
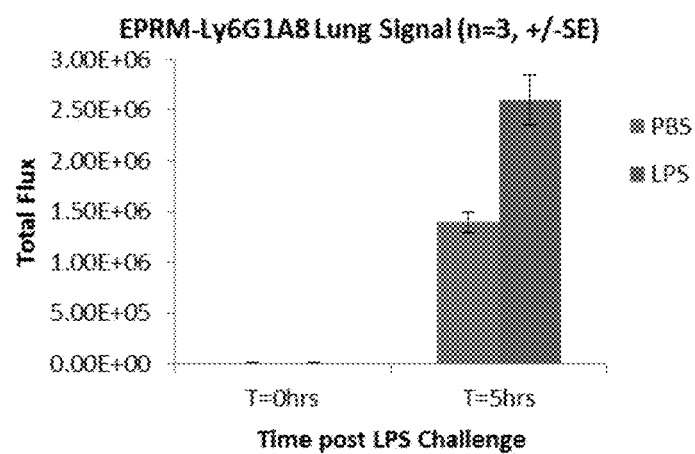
FIG. 6B is a graph showing luminescence signals measured for the same murine subjects as in FIG. 6A at two different times.

FIG. 6A shows images of the control group (left) and the LPS-challenged group (right) immediately after injection of the particles, and after 5 hours. FIG. 6B is a graph showing the relative measured luminescence flux for both groups at both t=0 and t=5 hours. The measured fluxes at t=5 hours show that detection of ROS in the lung tissues is readily achieved by the particles.

To compare luminescence signals from lung and liver tissues form the Ly6G-conjugated particles, BALB/cJ mice subjects were divided into two groups. One group was challenged with LPS (four 25 µL doses of 0.25 mg/mL followed by 25 µL PBS, delivered intratracheally) and the other (control) group was challenged with PBS (five 25 µL doses delivered intratracheally). Five hours post-challenge, the mice were injected intravenously with Ly6G1A8-conjugated particles (prepared as described above) and luminescence emission from the particles was imaged.

Figure 7A:
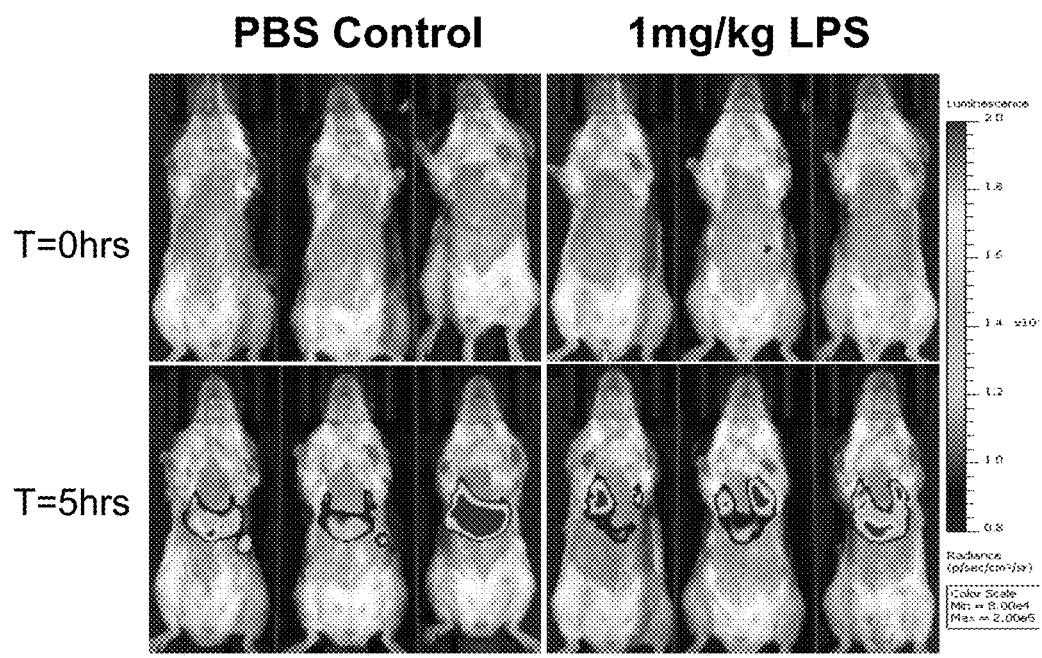
FIG. 7A is a series of images showing measured luminescence signals from antibody-conjugated particles in two groups of murine subjects.
Figure 7B:
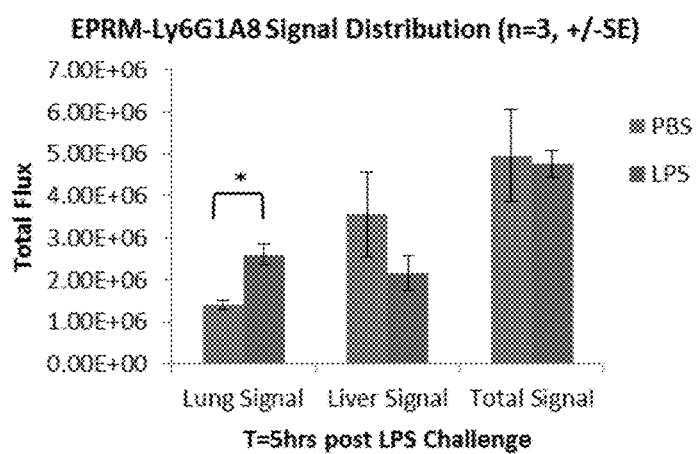
FIG. 7B is a graph showing luminescence signals measured from lung and liver tissue for the same murine subjects as in FIG. 7A.

FIG. 7A shows images of the control and LPS-challenged groups at t=0 and t=5 hours following particle injection. FIG. 7B is a graph showing the relative contributions to the measured luminescence signals for the control group (left bars) and LPS-challenged groups (right bars) for measured signals from lung tissues, liver tissues, and the total measured signal. For the control group, lung signals account for 28% of the measured luminescence, while liver signals account for the remaining 72%. However, for the LPS-challenged group, lung signals account for 55% of the measured luminescence, while liver signals account for the remaining 45%. Both groups have similar total measured luminescence fluxes. These results show that by using antibody-conjugated particles, luminescence signals from ROS in specific tissues can be selectively interrogated.

To investigate methods for further reducing luminescence signals due to liver tissues, two groups of BALB/cJ murine subjects were established. The first group was allowed normal access to food, while the second fasted for approximately 23 hours. Control and LPS-challenged groups were then constructed, with one fasting mouse and one mouse eating normally in each of the control and LPS-challenged groups. LPS challenges were performed with four 25 µL doses of 0.25 mg/mL LPS delivered intranasally, followed by 25 µL PBS. The mice of the control group were challenged with PBS (five 25 µL doses delivered intranasally). Five hours post-challenge, the mice were injected intravenously with Ly6G1A8-conjugated particles (prepared as described above) and luminescence emission from the particles was imaged.

Figure 8A:
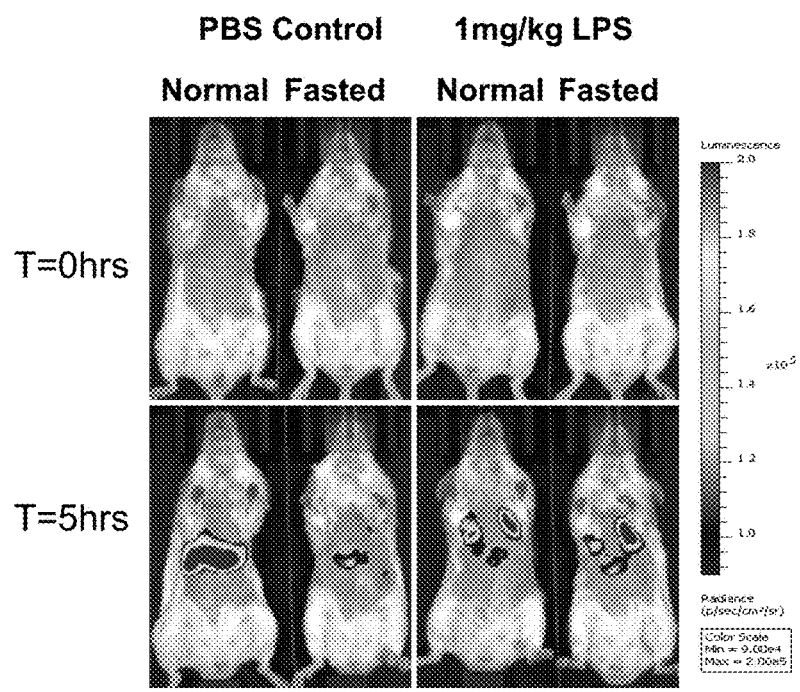
FIG. 8A is a series of images showing measured luminescence signals from antibody-conjugated particles in fasting and non-fasting murine subjects.
Figure 8B:
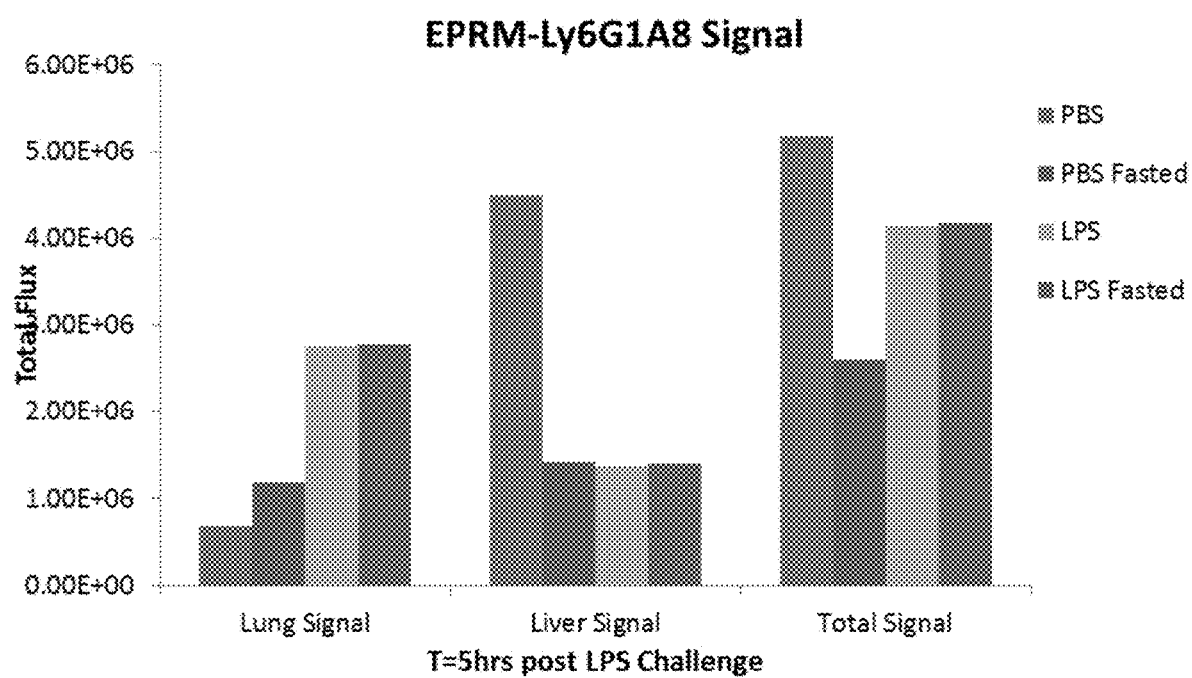
FIG. 8B is a graph showing luminescence signals measured from lung and liver tissue for the same murine subjects as in FIG. 8A.

FIG. 8A shows images of the normal-eating and fasting mice in the control and LPS-challenged groups as a function of time following injection of the particles. FIG. 8B is a graph showing contributions to each of the measured luminescence signals (lung signal, liver signal, and total signal) from each of the different types of mice in each of the control groups. In each grouping of bars in FIG. 8B, the contributions from left to right correspond to normal-eating control group mice, fasting control group mice, normal eating LPS-challenged mice, and fasting LPS-challenged mice. In the control group, which the mice ate normally, 87% of the measured luminescence signal was contributed by liver tissues, while 13% was contributed by lung tissues. Where the mice fasted, however, 54% of the measured signal was contributed by liver tissues, while 46% was contributed by lung tissues. Thus, in the control group, fasting significantly reduced the luminescence contributions from liver tissues, and is a viable method for improving the selective analysis of luminescence signals from tissues in a subject's body other than liver tissues.

For the LPS-challenged group, fasting had little effect on the relative contributions of liver and lung tissue-derived measured luminescence signals. However, for the LPS-challenged mice, the conjugated particles again selectively targeted lung tissues relative to liver tissues.

To investigate the detection sensitivity of europium- and terbium-based luminescent particles, a group of Swiss Webster mice were challenged with LPS (1 mg/kg delivered subcutaneously through the right thigh). The europium-based particles were prepared as described above. Terbium-based particles were prepared in a similar manner by substituting chelated europium with chelated terbium.

Induction of ROS activity was monitored at five hours post-challenge with subcutaneous injection of 75 µg of the terbium particles in the left thigh and 75 µg of the europium particles in the right thigh. Luminescence emission was imaged with no filter, with a 620 nm emission filter (the central wavelength of europium luminescence occurs at 614 nm), and with a 540 nm emission filter (the central wavelength of terbium emission occurs at 540 nm).

Figure 9A:
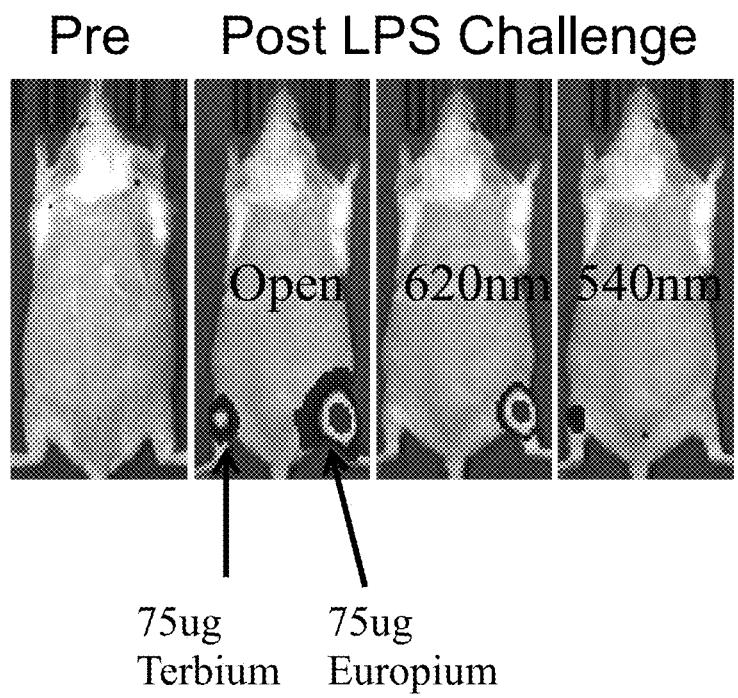
FIG. 9A is at set of images showing luminescence signals from particles with terbium or europium luminescent agents in a group of murine subjects.
Figure 9B:
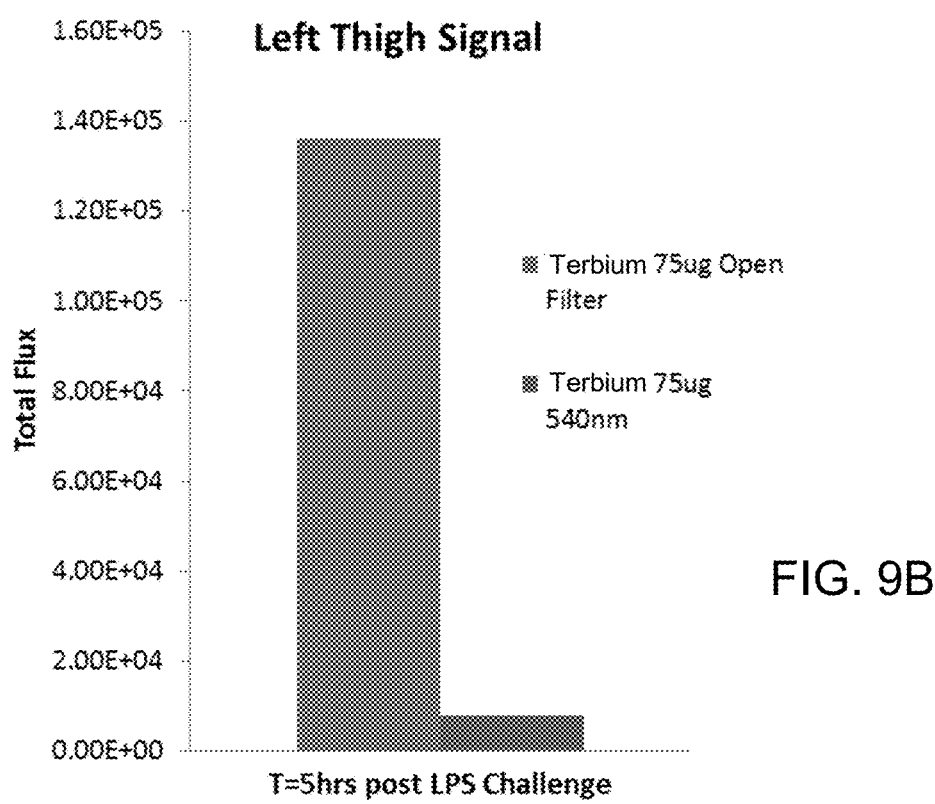
FIGS. 9B and 9C are graphs showing luminescence signals measured from the left and right thighs, respectively, of the same murine subjects as in FIG. 9A.
Figure 9C:
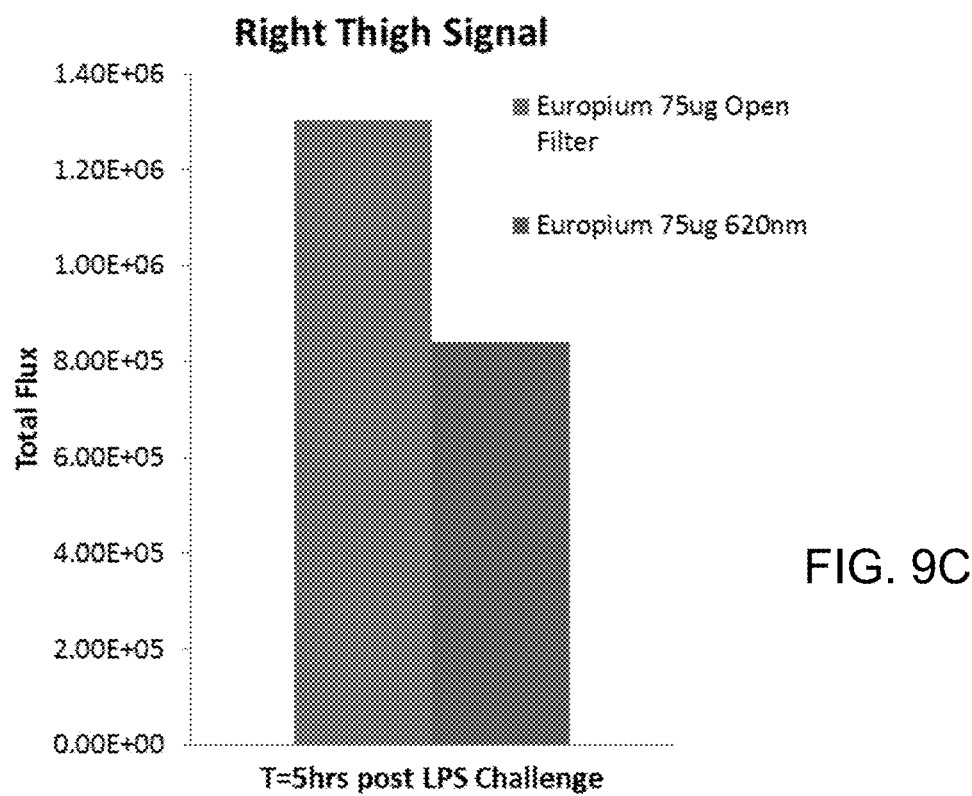

FIG. 9A shows a series of images of a murine subject before particle injection, and after particle injection under the three different filtering arrangements. FIGS. 9B and 9C are graphs showing quantification of the Tb and Eu luminescence signals from the left and right thigh, respectively. At a wavelength of 540 nm, the Tb signal level is only 6% of the total Tb luminescence signal (e.g., with no filter), while at a wavelength of 620 nm, the Eu signal level is 65% of the total Eu luminescence signal (e.g., with no filter).

OTHER EMBODIMENTS

A number of embodiments have been described. Nevertheless, it will be understood that various modifications may be made without departing from the scope of the disclosure. Accordingly, other embodiments are within the scope of the following claims.

What is claimed is:
1. A composition, comprising:
   a suspension medium; and
   a plurality of particles, wherein each one of the plurality of particles comprises:
      a core comprising at least one reacting group that reacts chemically with a reactive oxygen species in a subject, and at least one luminescent agent comprising at least one lanthanide element that emits luminescence in response to the reaction of the at least one reacting group;
      a first coating material encapsulating the core; and
      a second coating material encapsulating the first coating material and comprising at least one targeting group that binds to a structural entity in the subject.
2. The composition of claim 1, wherein the core comprises at least one of latex and polystyrene.
3. The composition of claim 1, wherein the first coating material comprises aminodextran and the second coating material comprises dextran aldehyde.
4. The composition of claim 1, wherein the at least one targeting group comprises at least one antibody.
5. The composition of claim 1, wherein the at least one lanthanide element comprises at least one of europium and terbium.
6. The composition of claim 1, wherein the at least one reacting group comprises thioxene or a thioxene derivative.
7. The composition of claim 1, wherein the plurality of particles comprises:
   a first subset of particles comprising a first targeting group, a first luminescent agent comprising at least one lanthanide element, and a first reacting group; and
   a second subset of particles comprising a second targeting group, a second luminescent agent comprising at least one lanthanide element, and a second reacting group,
   wherein the first and second targeting groups are different.
8. The composition of claim 7, wherein the first and second targeting groups comprise different antibodies.
9. The composition of claim 7, wherein the first and second luminescent agents are different.
10. The composition of claim 9, wherein the first and second luminescent agents comprise different lanthanide elements.
11. A kit for imaging reactive oxygen species in a living subject, the kit comprising:
   a housing; and
   positioned within the housing:
      a suspension medium; and
      a plurality of particles, wherein each one of the plurality of particles comprises:
         a core comprising at least one reacting group that reacts chemically with a reactive oxygen species in the living subject, and at least one luminescent agent
         comprising at least one lanthanide element that emits luminescence in response to the reaction of the at least one reacting group;
         a first coating material encapsulating the core; and
         a second coating material encapsulating the first coating material and comprising at least one targeting group that binds to a structural entity in the living subject.
12. The kit of claim 11, wherein:
   a first subset of the particles comprises a first targeting group, a first luminescent agent comprising at least one lanthanide element, and a first reacting group; and
   a second subset of the particles comprises a second targeting group, a second luminescent agent comprising at least one lanthanide element, and a second reacting group,
   wherein the first and second targeting groups are different.

13. The kit of claim 11, wherein the reactive oxygen species comprises at least one member selected from the group consisting of singlet oxygen, hydroxide radical, hypochlorous acid, superoxide radical, nitric oxide, and hydrogen peroxide.

* * * * *